United States Patent [19]
Kriesel

[11] Patent Number: 6,095,491
[45] Date of Patent: Aug. 1, 2000

[54] IN-LINE FLOW RATE CONTROL DEVICE

[75] Inventor: Marshall S. Kriesel, Saint Paul, Minn.

[73] Assignee: Science Incorporated, Bloomington, Minn.

[21] Appl. No.: 09/165,707

[22] Filed: Oct. 2, 1998

[51] Int. Cl.[7] .............................. F16K 25/00; F16K 35/00
[52] U.S. Cl. .......................... 251/206; 251/116; 137/355
[58] Field of Search .................................. 251/206, 113, 251/114, 116; 137/385

[56] References Cited

U.S. PATENT DOCUMENTS

| | | | | |
|---|---|---|---|---|
| 454,640 | 6/1891 | Farmer | .................................... | 251/113 |
| 562,410 | 6/1896 | Moon | ......................................... | 138/45 |
| 1,694,086 | 12/1928 | Waselak | .................................... | 251/116 |
| 2,780,833 | 2/1957 | Braunlich | ....................................... | 18/8 |
| 2,790,680 | 4/1957 | Rosholt | ..................................... | 299/105 |
| 3,136,341 | 6/1964 | Walker, Sr. et al. | ........................ | 138/45 |
| 4,724,869 | 2/1988 | Carter | ......................................... | 138/45 |
| 4,909,476 | 3/1990 | Messick | ................................... | 251/206 |
| 5,016,673 | 5/1991 | Carter et al. | ............................... | 138/89 |

*Primary Examiner*—Kevin Shaver
*Assistant Examiner*—David A Bonderer
*Attorney, Agent, or Firm*—James E. Brunton

[57] ABSTRACT

A readily adjustable flow rate control device having a movable flow control member which includes a plurality of spaced-apart flow restrictors which are adapted to be selectively positioned intermediate a fluid flow path extending between a fluid supply line and a fluid delivery line. The flow restrictors can take the form of porous rate control frits which can be selectively moved into index with the fluid flow path or microbores formed in a rotatable member which can be rotated to selectively move the microbores into index with the fluid flow path.

19 Claims, 4 Drawing Sheets

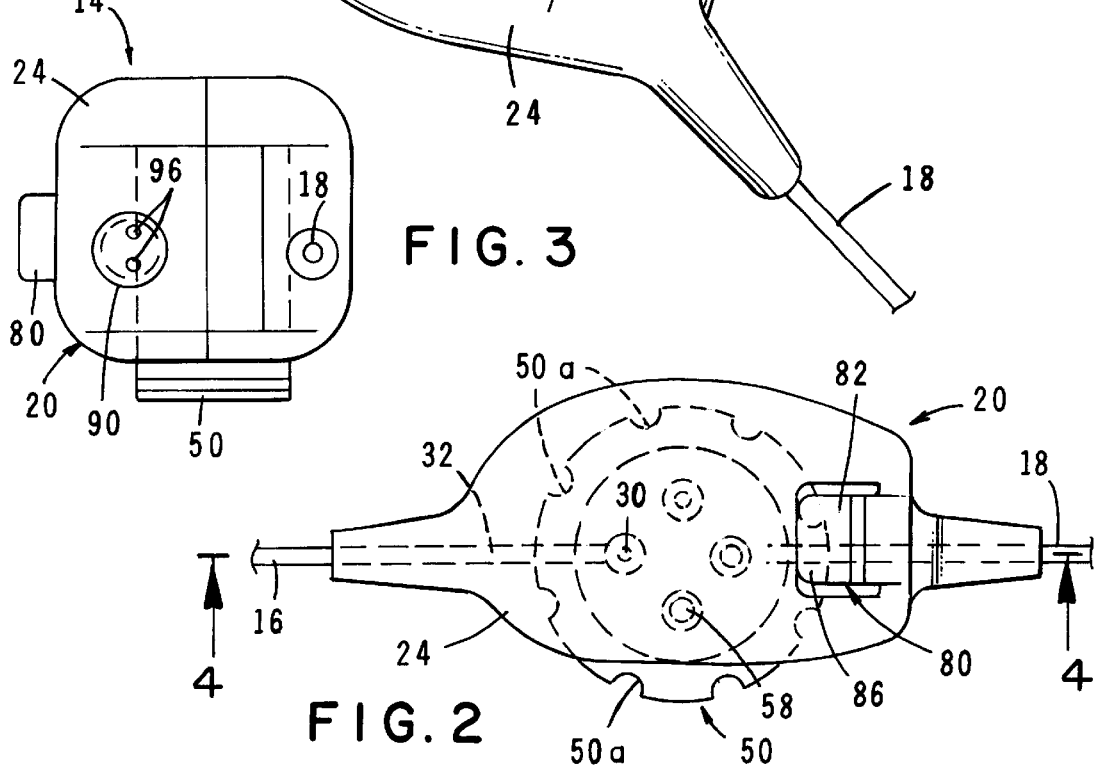

IN-LINE FLOW RATE CONTROL DEVICE

BACKGROUND OF THE INVENTION

1. Field of the Invention

The present invention relates generally to fluid flow rate control devices for controlling the rate of fluid flow from a fluid source to a remote location. More particularly, the invention concerns a novel, readily adjustable flow rate control device having a movable flow control member which includes a plurality of spaced-apart flow restrictors which are adapted to be selectively positioned intermediate a fluid supply line and a fluid delivery line.

2. Discussion of the Prior Art

A very large number of in-line fluid flow controllers for use in controlling the rate of fluid flow from a fluid supply line into a fluid delivery line have been suggested in the past. These types of devices are used in countless applications where it is necessary to control the rate at which fluid flows from a fluid source to a remote delivery point via fluid supply and delivery lines.

A frequently used application of prior art fluid flow devices is to control the rate of infusion of a fluid medicament from a source of fluid medicament into the body of a patient. Exemplary of such prior art devices those described in U.S. Pat. No. 5,499,968 issued to Milijasevic et al. This patent describes various constructions of in-line fluid flow controllers which are adapted for primarily use with a conventional fluid administration set of the type used for infusion of fluid into the body of a patient. In one embodiment, the Milijasevic et al fluid flow controllers comprise a housing, a chamber therein and an inlet to and an outlet from the chamber. The housing is adapted to receive therewithin at least one flow restrictor having an orifice configured to control the rate of fluid flow therethrough and into the body of the patient. In an alternate embodiment, the controller is adapted with a series of fluid passageways which are linked with a series of orifice plates held in position by a wedge.

Another somewhat similar prior art fluid flow rate control device is disclosed in U.S. Pat. No. 4,781,698 issued to Parren. The Parren device comprises a conventional roller clamp which is connected to a drop chamber. The drop chamber controls the size of the droplets flowing toward the roller clamp and the roller clamp controls the rate of fluid flow through the delivery line. The Parren apparatus includes a disk having a discharge opening which is selectively alignable with one or more drop tubes and includes a flexible edge or wiper means formed around the discharge opening to provide a seal between the disk and the selected drop tube to prevent fluid from seeping between the disk and the mounting plate.

A common drawback of many of the prior art flow controllers is that the controllers are often complex in construction, are difficult and costly to manufacture, are often somewhat unreliable and lack ease of adjustability to quickly and easily vary the rate of fluid through the device. The thrust of the present invention is to overcome these drawbacks and provide a compact, readily adjustable, highly precise flow rate control device which is easy to install within a fluid system is easy to use and is highly reliable.

SUMMARY OF THE INVENTION

It is an object of the present invention to provide a compact, easy-to-use flow rate control device which can be conveniently interposed within a single fluid flow plate extending between a fluid supply line and a fluid delivery line for precisely controlling the rate of fluid flow toward the delivery line.

More particularly, it is an object of the invention to provide a flow rate control device of the aforementioned character which can be conveniently inserted into an administration set of the character used for infusing fluids into the human body.

Another object of the invention is to provide a flow rate control device as described in the preceding paragraph which comprises a novel flow restrictor support member that carries a plurality of flow restrictors which can be selectively positioned within the path of the fluid flowing through the device.

Another object of the invention is to provide a flow rate control device of the type described in the preceding paragraph in which the flow restrictors comprise porous frits of varying porosity.

Another object of the present invention is to provide a flow rate control device of the class described in which the flow restrictors comprise laser drilled micro-bores of various sizes.

Another object of the invention is to provide a flow rate control device of the aforementioned character in which the flow restrictor support member is locked against movement until unlocked through the use of a specially designed physician's key.

BRIEF DESCRIPTION OF THE DRAWINGS

FIG. 1 is a generally perspective view of one form of the in-line flow rate control device of the invention.

FIG. 2 is a side view of the device.

FIG. 3 is a right-side view of the device.

DESCRIPTION OF THE INVENTION

Figure 4:
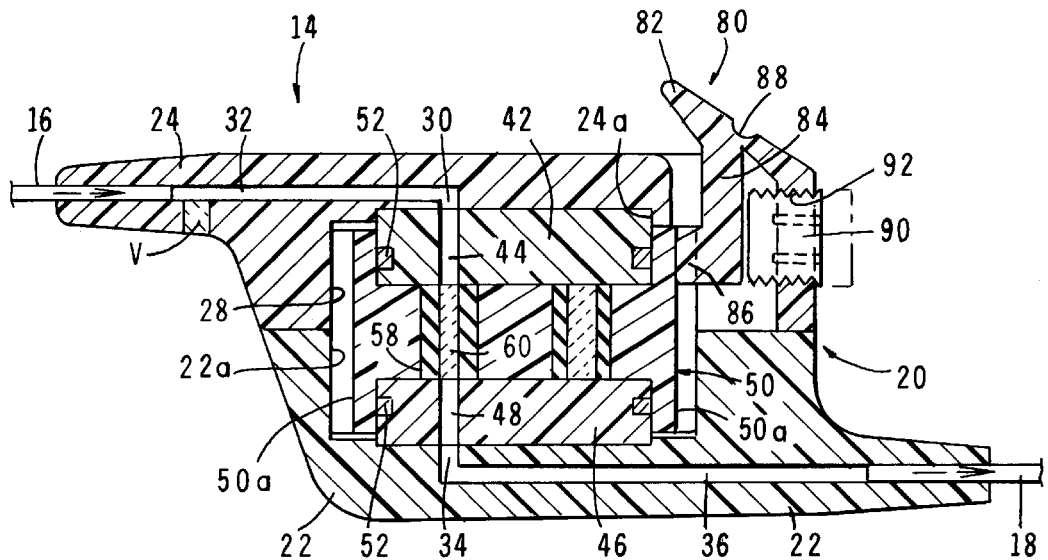
FIG. 4 is a cross-sectional view taken along lines 4—4 of FIG. 2.

Referring to the drawings and particularly to FIGS. 1 through 5, one form of the adjustable rate control device of the present invention is there illustrated and generally designated by the numeral 14. As illustrated in FIGS. 1 and 2, the device is adapted to be interposed between a fluid supply 16 line which is interconnected with a source of fluid under pressure (not shown) and a fluid delivery line 18 which can be interconnected with a remote site to which the fluid is to be delivered at a controlled rate.

Figure 6:
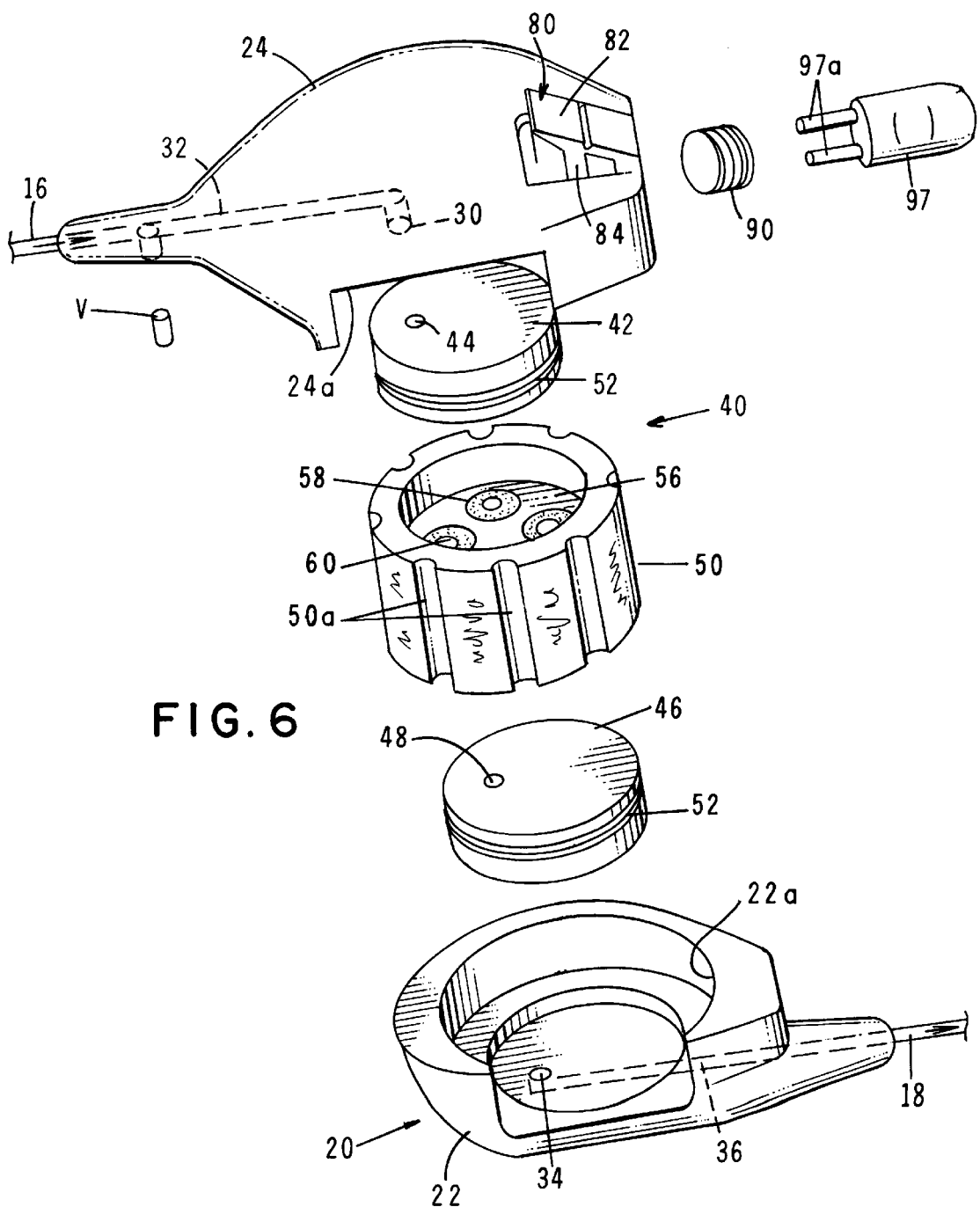
FIG. 6 is a generally perspective exploded view of the device shown in FIGS. 1 through 4.
Figure 7:
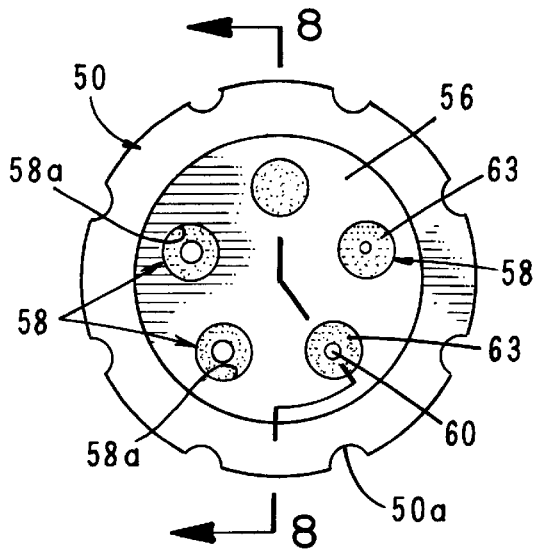
FIG. 7 is a front view of the rate control assembly of the device.

The device of the present form of the invention comprises a hollow housing 20 which is made up of a base portion 22 and an interconnected cover portion 24. As best seen in FIGS. 4 and 6, base portion 22 is provided with an internal cavity 22a and cover 24 is provided with an internal cavity 24a so that when the components are connected in the manner shown in FIGS. 1 through 4, an internal chamber 28 is formed. Chamber 28 has a fluid inlet 30 which is in communication with an inlet passageway 32 formed in cover 24, which, in turn, is in communication with supply line 16. Similarly, chamber 28 has a fluid outlet 34 which is in communication with an outlet passageway 36 formed in base 22 which, in turn, is in communication with delivery line 18.

The novel fluid rate control means of the invention is disposed within chamber 28 and here comprises an adjustable rate control mechanism 40 having a first hub portion 42 which includes a fluid passageway 44 that is in communication with inlet 30. Mechanism 40 also includes a second hub portion 46 which includes a passageway 48 that is in communication with outlet 34 and passageway 36. Rotatably carried by hub portions 42 and 46 is a control knob 50. O-rings 52 carried by hub portions 42 and 46 sealably engage control knob 50 and prevent leakage among the various cooperating components. As indicated in FIG. 4, hub portion 42 is bonded to cover 24 while hub portion 46 is bonded to base 22 and cover 24 is provided with a vent "V".

Figure 8:
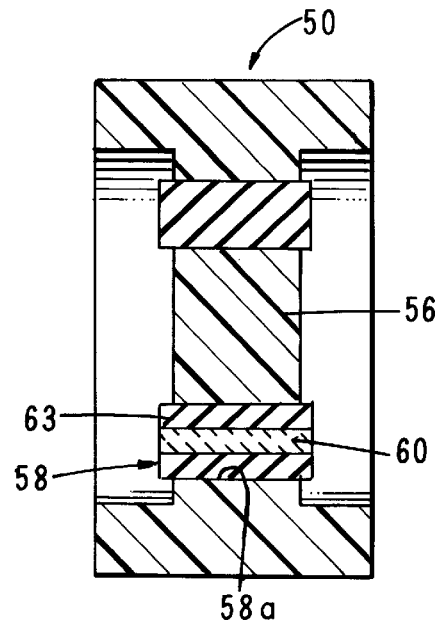
FIG. 8 is a view taken along lines 8—8 of FIG. 7.

Mounted within control knob 50 and rotatable therewith is a control member, here shown as a center wall 56. As shown in FIG. 8, wall 56 carries a plurality of circumferentially spaced apart flow restrictors 58 each of which can be selectively moved into index with flow passageways 44 and 48 by rotating knob 50 relative to housing 20.

In the embodiment of the invention shown in FIGS. 1 through 8, each flow restrictor 58 includes a porous rate control frit 60 (see FIGS. 7 and 8), which is secured in place within apertures 58a formed in member 56 by a moldable elastomer 63 (see FIG. 8). With the construction shown, by rotating knob 50 relative to housing 20, each of the rate control frits 60 can be moved sequentially into alignment with passageways 44 and 48. Because each of the frits 60 is of a different, preselected porosity, it is apparent that the rate of fluid flow outwardly of the device through delivery passageway 36 and delivery line 18 can be precisely contolled by interposing a particular frit in the fluid flow path.

Figure 9:
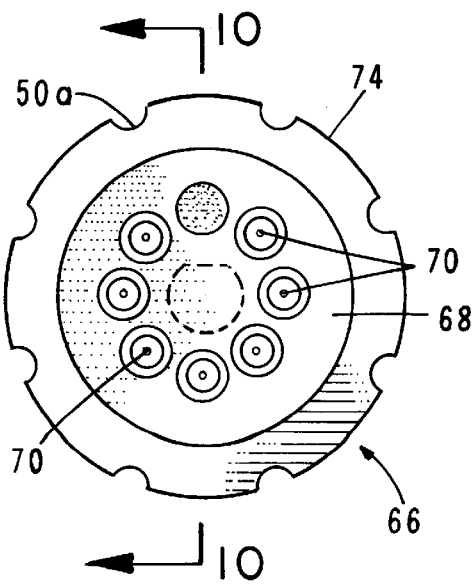
FIG. 9 is a front view of an alternate form of rate control member of the device.
Figure 10:
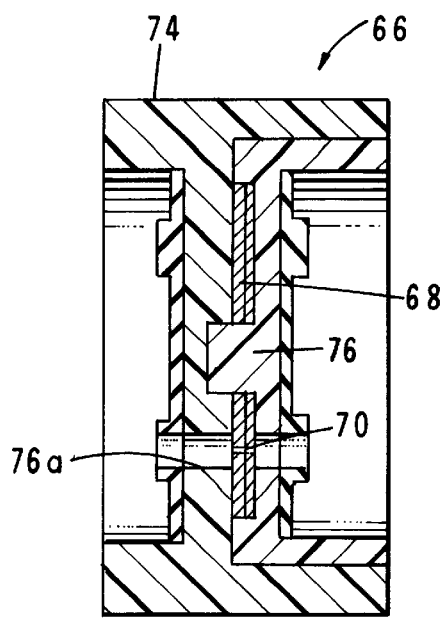
FIG. 10 is a cross-sectional view taken along lines 9—9 of FIG. 8.

Turning to FIGS. 9 and 10, an alternate form of rate control mechanism is there shown. This rate control mechanism 66 is similar in many respects to mechanism 40 and like numerals are used to identify like components. The major difference between mechanisms 40 and 66 resides in the differently configured control members. For example, the control member in this latest embodiment comprises a thin wafer 68 having a plurality of circumferentially spaced, laser-drilled microbores 70 (FIG. 9). Wafer 68 is carried interiorly of a slightly differently configured control knob assembly 74 which includes a central wall 76 that supports wafer or member 68. Central wall 76 is provided with apertures 76a, which align with microbores 70 so as to permit fluid flow therethrough. By rotating control knob assembly 74, a selected one of the laser drilled microbores 70 can be moved into alignment with passageways 44 and 46 formed in hubs 42 and 48. Accordingly, by selecting an aperture of a particular size, the rate of fluid flow toward outlet passageway 36 can be precisely controlled.

Figure 5:
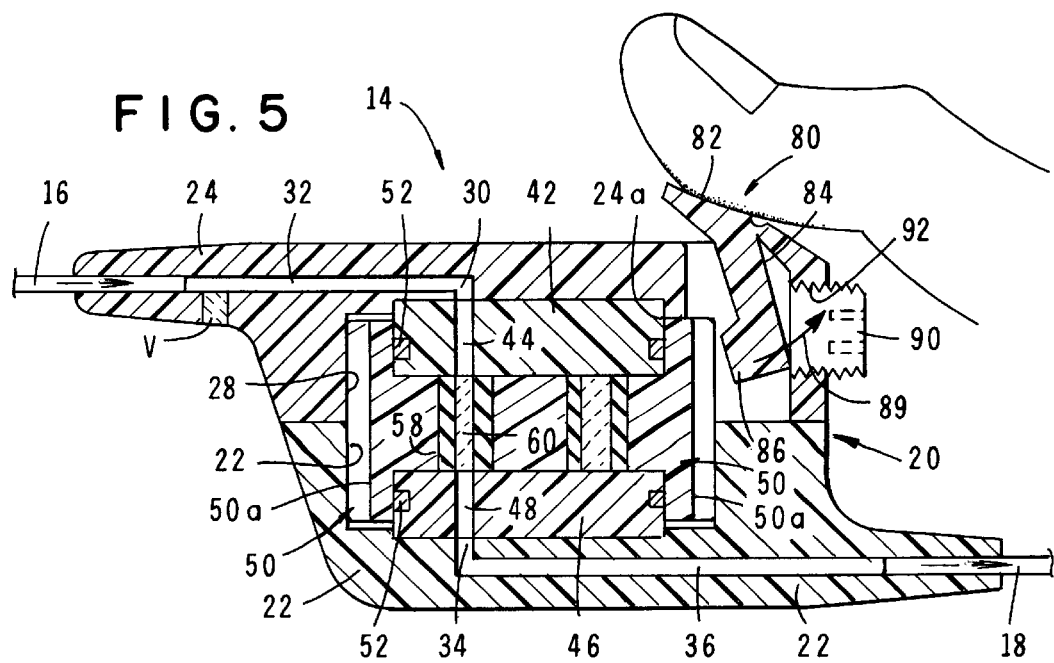
FIG. 5 is a cross-sectional view similar to FIG. 4, but illustrating the manner of operation of the locking means of the invention for preventing rotation of the rate control member of the apparatus.

Another important feature of the invention is the provision of locking means for releasably locking the control members or knobs 50 and 74 against rotation. As best seen by referring to FIG. 6, the control knobs are provided with a plurality of spaced-apart grooves 50a. In the embodiment of the invention shown in FIGS. 1 through 6, the locking means comprise a locking member 80 which is connected to housing 20 in the manner best seen in FIG. 4. Locking member 80 includes an upper finger engaging portion 82 which is integrally formed with a downwardly extending locking finger 84. Proximate the lower extremity of locking finger 84 is a protuberance 86 which is normally biased into engagement with one of the spaced apart grooves 50a formed in rotatable knob or control member 50. Provided intermediate the ends of finger engaging portion 82 is a living hinge portion 88 which permits the locking member to flex in the manner shown in FIG. 5 when a pressure is exerted on portion 82 by the finger of the user. More particularly, as shown in FIG. 5, when the forward portion of the finger engaging member is depressed, the locking finger will swing rearwardly in the direction of the arrow 89 in a manner to move the locking protuberance 86 thereof out of engagement with the control knob 50. With the locking position moved to the position shown in FIG. 5, the user can freely rotate the control knob in a manner to bring a selected rate control frit into alignment with passageways 44 and 48. The locking member is constructed of a yieldably deformable spring-like material so that when pressure is released on the finger engaging port ion 82, the member will automatically spring back to its original starting position as shown in FIG. 4 once again locking the control knob 50 against further rotation.

Another novel feature of the apparatus of the invention is the physician key operated locking means which functions to prevent movement of the locking finger of the locking means from the first position shown in FIG. 4 to the retracted position shown in FIG. 5. This latter means here comprises a externally threaded locking button 90 which is threadably received within an internally threaded opening 92 provided in housing 20. As best seen by referring to FIG. 3, locking button 90 is provided with a pair of spaced-apart spanner wrench receiving openings 96 which are adapted to receive outwardly extending pins 97a of a physician's key 97 which is of the character shown in FIG. 6 of the drawings. This physician's key which is identified by the numeral 97 can be used to threadably move button 90 relative to housing 20 either into or out of engagement with locking finger 84. When the locking button 90 is threaded inwardly of the housing into engagement with locking finger 84, the control knob 50 will remain in the locked position unless and until the physician or other care giver having possession of the physician's key and use the key to move locking button 90 into the retracted position shown in FIG. 5.

Using the apparatus of the invention, the rate control device is interposed between the supply line and the delivery line in the manner shown in FIG. 1. Next, the physician or care giver using the physician key 97 will threadably retract locking button 90 into the position shown in FIG. 5. The pressure exerted on finger engaging member 82 of the locking mean s will then move the locking finger into the retracted position shown in FIG. 5 permitting the care giver to rotate control knob 50 so as to position the desired flow restrictor in line with the fluid flow path. In this regard, it is to be noted that knob 50 is provided with indicating indicia of the character shown in FIG. 1 which indicate to the care giver the flow rate through the device permitted by the flow restrictor which has been moved into alignment with the fluid flow path through the device. Once the flow rate has been set by the care giver, the release of finger engaging member 82 will cause the locking finger of the locking means to once again return to the locking position shown in FIG. 4 thereby preventing further rotation of the control knob. By rotating button 90 threadably inwardly of the housing into engagement with locking finger 86, unauthorized rotation of the rate control knob 50 is positively prevented.

With the rate control set in the manner described in the preceding paragraphs, fluid flowing through supply line 16 will flow into the device through passageway 32, into passageway 44 formed in hub member 42, and then through the rate control frit 60 which has been moved into alignment with passageway 44. After flowing through passageway 48, the fluid will next flow into passageway 34, then into passageway 36 formed in base member 22 and finally into the delivery line 18 which may be connected to a remote site such as an infusion cannula or the like. So long as fluid is flowing inwardly of the device through the supply line 16, the rate of fluid flow outwardly of the device through delivery line 18 will be precisely controlled by the novel rate control means of the invention.

Having now described the invention in detail in accordance with the requirements of the patent statutes, those skilled in this art will have no difficulty in making changes and modification in the individual parts or their relative assembly in order to meet specific requirements or conditions. Such changes and modifications may be made without departing from the scope and spirit of the invention, as set forth in the following claims.

I claim:

1. A flow rate control device for controlling the rate of fluid flow between a fluid supply line connected to a source of fluid and a fluid delivery line, said flow rate control device comprising:

(a) a housing having walls defining an internal chamber, said internal chamber having an inlet in communication with said fluid supply line, an outlet in communication with said fluid delivery line and a flow path between said inlet and said outlet; and (b) flow rate control means disposed within said housing between said inlet and said outlet for controlling the rate of fluid flow through said flow path, said flow rate control means comprising an assemblage rotatably connected to said housing, said assemblage including an annular shaped knob having a peripheral surface and a center wall disposed within said annular shaped knob, said center wall having a first and second circumferentially spaced apart flow restrictors, said assemblage being rotatable from a first position wherein said first flow restrictor is aligned with said inlet and a second position wherein said second flow restrictor is aligned with said inlet.

2. The device as defined in claim 1 in which said first and second flow restrictors comprise first and second spaced apart, porous frits mounted on said center wall.

3. The device as defined in claim 1 in which said first and second flow restrictors comprise circumferentially spaced apart apertured wafers carried by said center wall.

4. The device as defined in claim 1 further including locking means carried by said housing for releasably locking said control member against rotation.

5. The device as defined in claim 4 in which said peripheral surface of said knob is provided with a plurality of spaced apart grooves and in which said locking means comprises a locking member connected to said housing, said locking member including:

(a) a locking finger normally disposed within a selected one of said grooves formed in said peripheral surface of said knob; and (b) release means operably associated with said locking finger for moving said locking finger out of said one of said selected grooves formed in said peripheral surface of said knob.

6. The device as defined in claim 5 in which said release means comprises a finger engaging member connected to said locking finger, said finger engaging means being movable from a first extended position into a second depressed position wherein said locking finger is moved out of engagement with said one of said selected grooves formed in said peripheral surface of said knob.

7. The device as defined in claim 6 in which said locking means further comprises lock-out means carried by said housing for preventing movement of said locking finger by said finger engaging member.

8. The device as defined in claim 7 in which said lock-out means comprises a threaded lock-out button which is theadably connected to said housing proximate said locking finger for movement between a first position in engagement with said locking finger to a second position spaced apart from said locking finger.

9. A flow rate control device for controlling the rate of fluid flow between a fluid supply line connected to a source of fluid and a fluid delivery line, said flow rate control device comprising:

(a) a housing having walls defining an internal chamber, said internal chamber having an inlet in communication with said fluid supply line and an outlet in communication with said fluid delivery line;

(b) flow rate control means disposed within said housing between said inlet and said outlet for controlling the rate of fluid flow from said inlet toward said outlet said flow rate control means comprising an assemblage rotatably connected to said housing, said assemblage including an annular shaped knob having a peripheral surface and a center wall disposed within said annular shaped knob, said center wall having a first and second circumferentially spaced apart flow restrictors, said control member being rotatable from a first position wherein said first flow restrictor is aligned with said inlet and a second position wherein said second flow restrictor is aligned with said inlet; and (c) locking means carried by said housing for releasably locking said annular shaped knob against rotation.

10. The device as defined in claim 9 in which said first and second flow restrictors comprise first and second spaced apart, porous frits mounted on said center wall.

11. The device as defined in claim 9 in which said first and second flow restrictors comprise circumferentially space-apart apertured wafers carried by said center wall.

12. The device as defined in claim 9 in which said peripheral surface of said knob is provided with a plurality of spaced apart grooves and in which said locking means comprises a locking member connected to said housing, said locking member including:

(a) a locking finger normally disposed within a selected one of said grooves formed in said peripheral surface of said knob; and (b) release means operably associated with said locking finger for moving said locking finger out of said one of said selected grooves formed in said peripheral surface of said knob.

13. The device as defined in claim 12 in which said release means comprises a finger engaging member connected to said locking finger, said finger engaging means being movable from a first extended position into a second depressed position wherein said locking finger is moved out of engagement with said one of said selected grooves formed in said peripheral surface of said knob.

14. The device as defined in claim 13 in which said locking means further comprises lock-out means carried by said housing for preventing movement of said locking finger by said finger engaging member.

15. The device as defined in claim 14 in which said lock-out means comprises a threaded lock-out button which is theadably connected to said housing proximate said locking finger for movement between a first position in engagement with said locking finger to a second position spaced apart from said locking finger.

16. The device as defined in claim 15 in which said lock-out means comprises a physician's key for engagement with said lock-out button to move said lock-out button between said first and second positions.

17. A flow rate control device for controlling the rate of fluid flow between a fluid supply line connected to a source of fluid and a fluid delivery line, said flow rate control device comprising:

(a) a housing having walls defining an internal chamber, said internal chamber having an inlet in communication with said fluid supply line, an outlet in communication with said fluid delivery line and a flow path between said inlet and said outlet; and (b) flow rate control means disposed within said housing between said inlet and said outlet for controlling the rate of fluid flow through said flow path, said flow rate control means comprising an assemblage rotatably connected to said housing, said assemblage including a member having a peripheral surface and an interior wall connected to said member, said wall having a first and second spaced apart flow restrictors, said assemblage being rotatable from a first position wherein said first flow restrictor is aligned with said inlet and a second position wherein said second flow restrictor is aligned with said inlet.

18. The device as defined in claim 17 further including locking means carried by said housing for releasably locking said assemblage against rotation.

19. The device as defined in claim 18 in which said peripheral surface of said member is provided with a plurality of spaced-apart grooves and in which said locking means comprises a locking member connected to said housing, said locking member including:

(a) a locking finger normally disposed within a selected one of said grooves formed in said peripheral surface of said member; and (b) release means operably associated with said locking finger for moving said locking finger out of said one of said selected grooves formed in said peripheral surface of said member.

* * * * *